US 11,166,737 B2

(12) United States Patent
Iwasaki

(10) Patent No.: US 11,166,737 B2
(45) Date of Patent: Nov. 9, 2021

(54) BASKET TYPE TREATMENT TOOL

(71) Applicant: OLYMPUS CORPORATION, Hachioji (JP)

(72) Inventor: Nobuyoshi Iwasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 214 days.

(21) Appl. No.: 16/449,564

(22) Filed: Jun. 24, 2019

(65) Prior Publication Data

US 2019/0321060 A1 Oct. 24, 2019

Related U.S. Application Data

(63) Continuation of application No. PCT/JP2016/088662, filed on Dec. 26, 2016.

(51) Int. Cl.
*A61B 17/221* (2006.01)
*A61B 17/00* (2006.01)

(52) U.S. Cl.
CPC .. *A61B 17/221* (2013.01); *A61B 2017/00336* (2013.01); *A61B 2017/00818* (2013.01); *A61B 2017/2212* (2013.01)

(58) Field of Classification Search
CPC .......... A61B 17/221; A61B 2017/2212; A61B 1/0008; A61B 1/00085; A61B 1/00098;
(Continued)

(56) References Cited

U.S. PATENT DOCUMENTS 5,462,553 A * 10/1995 Dolgin ............. A61B 17/32056
606/110
6,673,080 B2 * 1/2004 Reynolds ......... A61B 17/00234
606/113
(Continued)

FOREIGN PATENT DOCUMENTS

| DE | 102005030010 A1 | 12/2006 | |
| EP | 3069667 A1 | 9/2016 | |
| JP | S61-284239 A | 12/1986 | |
| JP | H10-165406 A | 6/1998 | |
| JP | 2006314714 A * | 11/2006 | ........... A61B 17/221 |
| JP | 2013-022386 A | 2/2013 | |

(Continued)

OTHER PUBLICATIONS

JP2006314714A-Lithomyl—Google Patents—English Translation—accessed Mar. 17, 2021 from https://patents.google.com/patent/JP2006314714A/en?oq=JP+2006314714+A (Year: 2021).*
(Continued)

*Primary Examiner* — Wade Miles
*Assistant Examiner* — Kankindi Rwego
(74) *Attorney, Agent, or Firm* — Oliff PLC

(57) ABSTRACT

A basket type treatment tool includes a sheath, a distal end cover attached to a distal end of the sheath and having grooves including first and second grooves, basket wires, and an operating wire, the first groove has first surface in which at least part of bottom surface of the first groove is inclined in a direction along the basket wires that are in a state in which the basket protrudes from the distal end cover, the second groove has second surface in which at least part of bottom surface of the second groove is inclined in a direction along the basket wires, and when the operating wire is pulled through a different one of the plurality of groove sections and abuts one of the first surface and one of the second surface.

14 Claims, 10 Drawing Sheets

(58) Field of Classification Search
CPC .......... A61B 1/00101; A61B 17/00234; A61B 17/0057; A61B 2017/00336; A61B 2017/00818; A61M 25/00; A61M 25/0067; A61M 25/0082; A61F 2/00; A61F 2/01; A61F 2/011; A61F 2/013; A61F 2/24; A61F 2/2427; A61F 2/243; A61F 2/2433; A61F 2/2436; A61F 2/95; A61F 2/9522; A61F 2002/015; A61F 2002/016; A61F 2002/018
USPC .................................. 600/101, 107; 606/127
See application file for complete search history.

(56) References Cited

U.S. PATENT DOCUMENTS

| | | | |
|---|---|---|---|
| 2004/0138677 A1 | 7/2004 | Little et al. | |
| 2014/0121458 A1* | 5/2014 | St. George | A61B 1/00085 600/107 |

FOREIGN PATENT DOCUMENTS

| | | |
|---|---|---|
| WO | 2015/072366 A1 | 5/2015 |
| WO | 2016/151931 A1 | 9/2016 |

OTHER PUBLICATIONS

Mar. 21, 2017 International Search Report issued in International Patent Application No. PCT/JP2016/088662.

* cited by examiner

BASKET TYPE TREATMENT TOOL

The present invention relates to a basket type treatment tool. This application is a continuation application based on PCT Patent Application No. PCT/JP2016/088662 filed Dec. 26, 2016, the content of which is incorporated herein by reference.

BACKGROUND

Basket type grasping forceps can configured to be inserted into a duct in the body such as the bile duct or the like and collect foreign substances such as calculi or the like is known (for example, see Japanese Unexamined Patent Application, First Publication No. 2013-22386). Since a basket type grasping forceps has a structure configured to hold foreign substances using a plurality of wires, when a large foreign substance is collected, a basket may not be able to be removed from a duct while holding the foreign substances in some cases. For example, when foreign substances do not come off between the pluralities of wires, the basket may not be able to be removed from the duct.

SUMMARY

A basket type treatment tool can include a sheath extending in a longitudinal axis direction and a distal end cover. The distal end cover can be a tubular member attached to a distal end of the sheath, and it can have a plurality of grooves passing through an inner circumferential surface and an outer circumferential surface. The plurality of grooves can be formed in a concave shape. The tool can also include plurality of basket wires that are configured to extend and retract from the distal end cover to form a basket that is able to expand and contract. The tool can also include an operating wire connected to proximal ends of the plurality of basket wires and inserted into the sheath to advance and retract. The plurality of groove sections have first groove and second grooves disposed to be separated from the first groove in a circumferential direction of the distal end cover, the first groove has first surface that is inclined in the same direction that the basket wires are inclined in a state in which the basket protrudes from the distal end cover, the second groove has second surface that is inclined in the same direction the basket wires are inclined in a state in which the basket protrudes from the distal end cover. At least part of the bottom surface of the second groove has a shape different from the first surface, and when the operating wire is pulled from the distal end toward the proximal end of the sheath, each of the plurality of basket wires is pulled through a different one of the plurality of groove sections and abuts one of the first surface and one of the second surface.

In the basket type treatment tool, the second surface may be formed to be chamfered to have a second chamfering amount smaller than a first chamfering amount of the first surface, and among the plurality of basket wires, a basket wire in contact with the second surface may be configured to break earlier than a basket wire in contact with the first surface.

In the basket type treatment tool, the second chamfering amount may be half or less than half of the first chamfering amount.

In the basket type treatment tool, the number of second grooves may be two or more, and the second grooves may be formed at positions neighboring each other in the circumferential direction.

In the basket type treatment tool, the number of the grooves may be equal to the number of the basket wires.

In the basket type treatment tool, the first surface and the second surface may be slopes inclined from the bottom surfaces of the first groove toward an inner circumferential surface of the distal end cover in a longitudinal axis direction of the distal end cover.

In the basket type treatment tool, the first surface may be formed by at least an inner circumferential surface side of the distal end cover among the bottom surface of the first groove being chamfered, and the second surface may be chamfered such that the bottom surface of the second groove on at least the inner circumferential surface side of the distal end cover may have a shape different from the first surface.

In the basket type treatment tool, when the operating wire is pulled in a direction from the distal end toward the proximal end of the sheath in a state in which a treatment object is accommodated in the basket, each of the plurality of basket wires may be pulled through a different one of the plurality of groove sections, and a breaking force of the basket wire may be different on the first surface and the second surface with which the plurality of basket wires abut.

DETAILED DESCRIPTION

Figure 1:
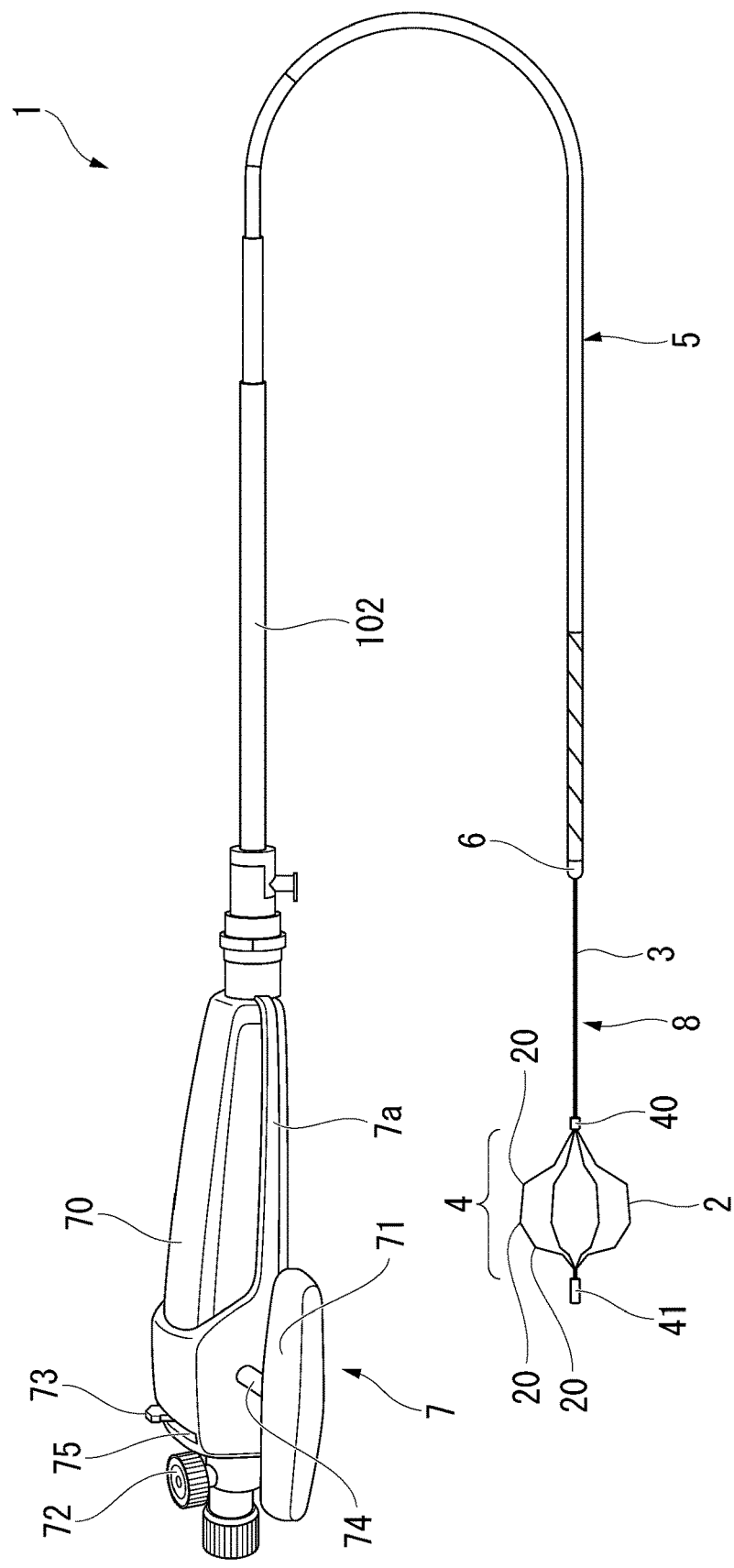
FIG. 1 is a general view of a basket type treatment tool according to an exemplary embodiment.

In an exemplary embodiment, a basket type treatment tool (hereinafter, simply referred to as "a treatment tool") 1 will be described. FIG. 1 is a general view of the treatment tool 1. A side of the treatment tool 1 in a lengthwise direction, on which a basket is provided, can be referred to as a distal side, and a side opposite to the distal side can be referred to as a proximal side.

As shown in FIG. 1, the treatment tool 1 includes a flexible sheath (hereinafter, simply referred to as "a sheath") 5, an operation section 7 and a treatment tool main body 8.

The operation section 7 is provided on a proximal end of the sheath 5, and includes an operation section main body 70, a handle 71, a wire connecting button 72 and a switching slider 73.

The operation section main body 70 functions as a housing for various operating mechanisms and a gripping section for an operator. While not shown, a movable mechanism or the like connected to the handle 71 or the wire connecting button 72, in addition to a communication path through which an operating wire 3 is inserted and an engaging section engaged with the operating wire 3, is accommodated in the operation section main body 70. The handle 71 is provided to be operated rotatably around a rotary shaft 74. The rotary shaft 74 has a pinion (not shown) formed at an end portion thereof disposed in the operation section main body 70. A proximal end portion of an operating wire having a rack (not shown) is connected to an engaging section in the operation section main body 70. According to a rotating operation of the handle 71, the rack advances and retracts with respect to the operation section main body 70, an engaging section moves according to movement of the rack, and the proximal end portion of the operating wire 3 is configured to movable. Further, the engaging section need not necessarily be directly connected to the proximal end portion of the operating wire 3 and may be connected to the engaging section via a rod connected to the proximal end portion of the operating wire 3.

The switching slider 73 is provided slidably in a slit 75 of the operation section main body 70, and configured to switch between a state in which the handle 71 may be operated such that it rotates in only one direction and a state in which the handle 71 may be rotatable in both directions according to a position of the switching slider 73.

The wire connecting button 72 is a button configured to switch between a state in which the proximal end portion of the operating wire 3 is engaged with an operating wire engaging section and a state in which the engagement is released.

Figure 2:
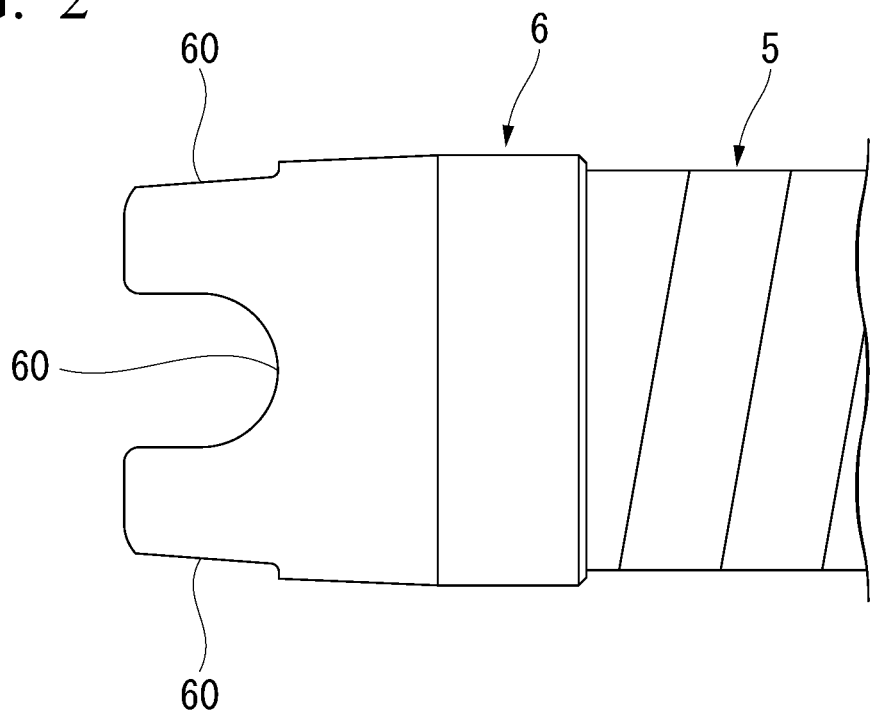
FIG. 2 is a side view showing a distal end portion of a sheath of the basket type treatment tool according to an exemplary embodiment.
Figure 3:
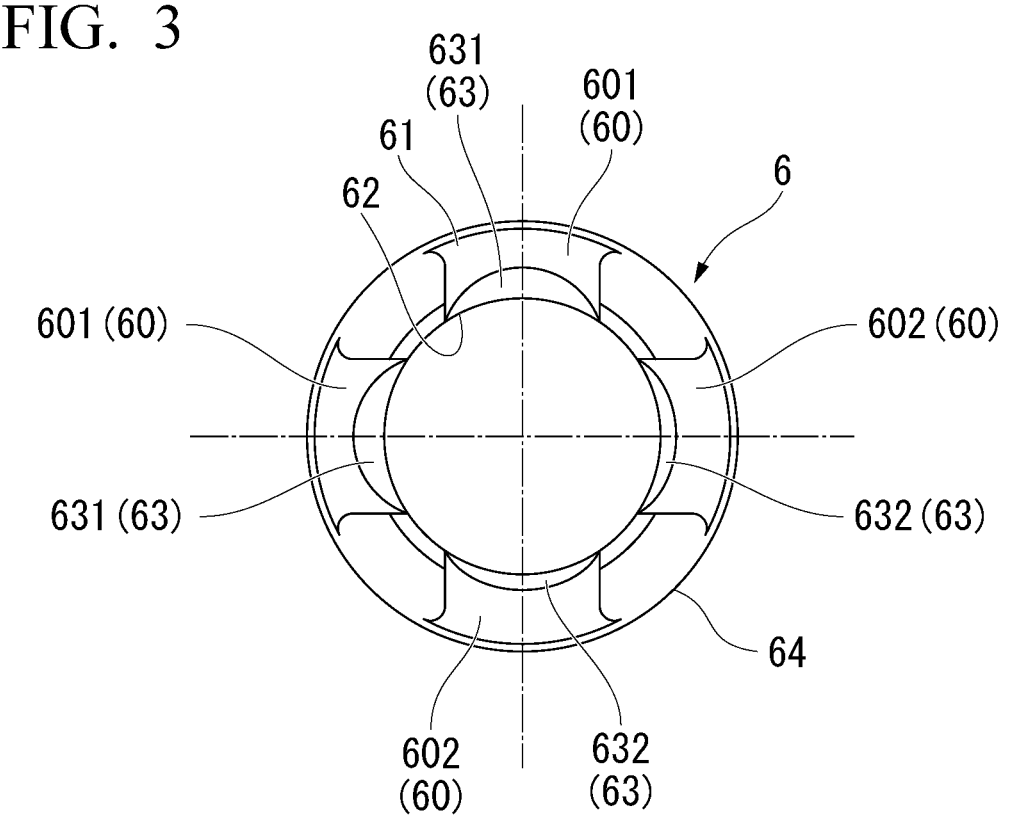
FIG. 3 is a front view of a distal end cover of an exemplary embodiment.
Figure 4:
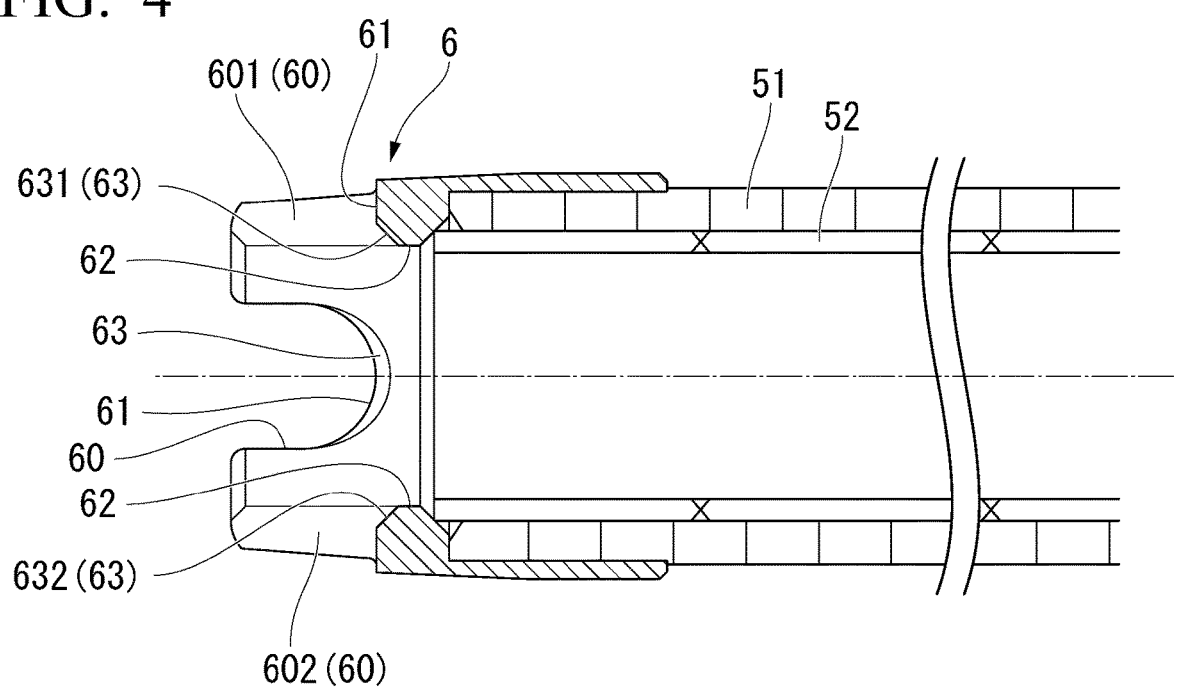
FIG. 4 is a cross-sectional view of the distal end portion of the sheath of the embodiment of the present invention.

FIG. 2 is a side view showing a distal end portion of the sheath 5. FIG. 3 is a front view of a distal end cover when seen from a distal side. FIG. 4 is a cross-sectional view of the distal end portion of the sheath. The sheath 5 may be configured by appropriately selecting a known resin material such as fluororesin, a thermoplastic elastomer, or the like, or a combination thereof, a coil sheath formed by winding a metal strand, a braid using a metal wire, and so on. As shown in FIG. 4, the sheath 5 of the embodiment is a sheath of a two-layer structure in which a resin tube 52 is provided inside a coil sheath 51.

A distal end cover 6 is fixed to a distal end portion of the sheath 5 by brazing, laser welding, or the like. The distal end cover 6 is a cylindrical member formed of a metal. Grooves 60 in which basket wires can be accommodated are formed in the distal end portion of the distal end cover 6. Preferably, the number of the grooves 60 coincides with the number of the basket wires.

As shown in FIGS. 2 to 4, each of the grooves 60 is formed to be a concave shape from a distal end to a proximal end and opening through in a thickness direction (opening between an inner circumferential surface 62 and an outer circumferential surface 64 of the distal end cover 6). Preferably, the grooves 60 are formed with uniform intervals therebetween in the circumferential direction. As shown in FIGS. 3 and 4, the plurality of grooves 60 are chamfered to form slopes 63 which are inclined from bottom sections (bottom surfaces) 61 of the grooves 60 toward the inner circumferential surface 62 in the longitudinal axis direction of the distal end cover 6. The plurality of grooves 60 are constituted by first grooves 601 and second grooves 602 having different form of chamfering of the slopes 63 on the side of the inner circumferential surface 62 of the distal end cover 6. Hereinafter, the slopes of the first grooves 601 are referred to as first surfaces 631, and slopes of the second grooves 602 are referred to as second surfaces 632.

Form of chamfering of the slopes 63 disclosed herein refer to parameters that contribute to a breaking force for breaking the basket wires and characterize the slopes, for example, shapes, inclination angles, lengths, chamfering amounts, and so on, of the slopes 63. These parameters are different from each other for the slope 63 (the first surfaces 631) of the first grooves 601 and the slopes 63 (the second surfaces 632) of the second grooves 602.

Figure 5A:
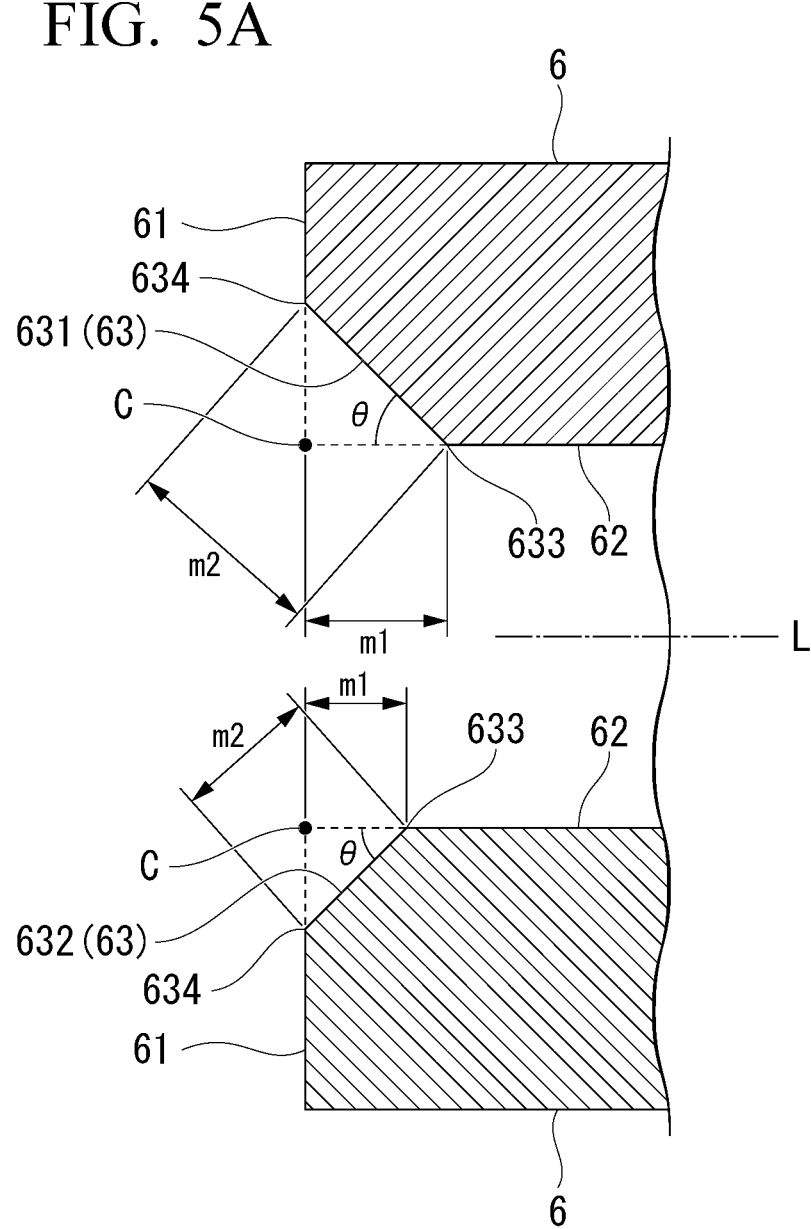
FIG. 5A is a schematic view showing a form of chamfering of a slope.
Figure 5B:
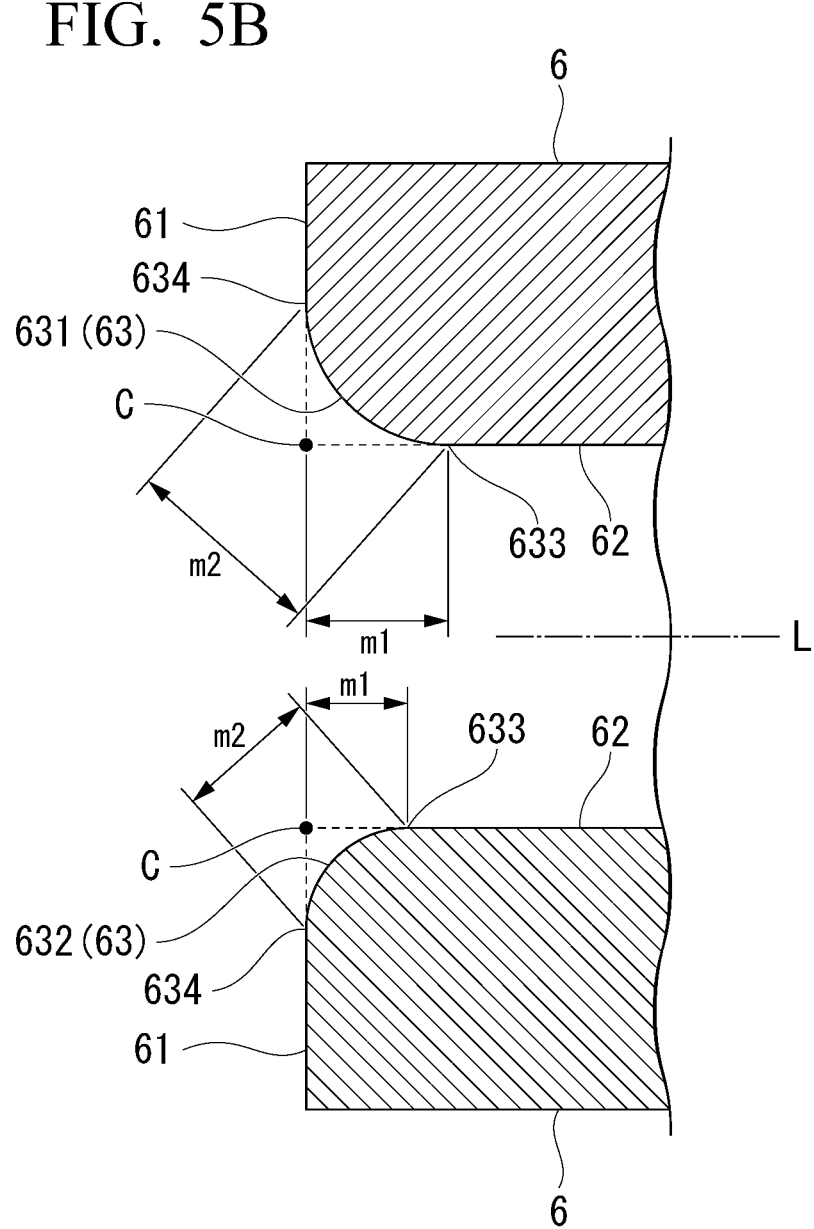
FIG. 5B is a schematic view showing the form of chamfering of the slope.

FIGS. 5A and 5B are schematic views showing the form of chamfering of the slopes 63. As shown in FIGS. 5A and 5B, the inclination angle of the slopes 63 represents an inclination angle $\theta$ of the slopes 63 with respect to the inner circumferential surface 62 of the distal end cover 6 (a center axis of the sheath 5) in a cross section in a longitudinal axis direction (a center axis direction) L. As shown in FIGS. 5A and 5B, a distance m represents a distance that is an element in the longitudinal axis direction L of the slopes 63 in the cross section in the longitudinal axis direction L (a length from a position at which the inner circumferential surface 62 and the slopes 63 of the distal end cover 6 intersect each other to a point C that is a virtual corner section shown in FIG. 5A). As shown in FIGS. 5A and 5B, a distance m2 represents the shortness distance that connects a proximal end 633 and a distal end 634 of the slope 63 in the cross section in the longitudinal axis direction L. When the shapes of the slopes 63 are different from each other, specifically, at least one of the inclination angle $\theta$ and the distances m1 and m2 is smaller on the second surfaces 632 than on the first surface 631. For example, there is a case in which the chamfering amount of the second surfaces 632 is smaller than the chamfering amount of the first surface 631, or the like. Further, the chamfering disclosed herein may be a surface including C chamfering or R chamfering and not including a point (an edge of an inner circumferential surface of the distal end cover 6) that has a virtual corner section C (see FIGS. 5A and 5B). The first surfaces 631 and the second surfaces 632 extend in a direction in away from a center axis L of the sheath 5 from the proximal side toward the distal side of the distal end cover 6 in a direction in which basket wires 2 extend.

A method of realizing a chamfering amount disclosed herein is not limited to processing of grinding the corner sections C between the bottom sections 61 and the inner circumferential surfaces 62 of the grooves 60. For example, also in a slope formed using other methods such as a distal end cover or the like molded using a mold material, a form of chamfering of each slope can be specified based on the above-mentioned concept.

In the embodiment, as shown in FIG. 3, in four grooves 60, two first grooves 601 and two second grooves 602 are formed. In the disposition of the first grooves 601 and the second grooves 602, for example, the two first grooves 601 are provided adjacent to each other and the two second grooves 602 are provided adjacent to each other in the circumferential direction of the distal end cover 6.

In the embodiment, as shown in FIG. 4, any one of the first surfaces 631 and the second surfaces 632 has a C surface having an the inclination angle $\theta$ of 45 degrees, lengths of the slopes 63 (length corresponding to a length m2 shown in FIG. 5A) are different from each other, and chamfering amount of the first surfaces 631 are larger than that of the second surfaces 632. More specifically, chamfering amount of the second surfaces 632 (a second chamfering amount) are ½ or less of chamfering amount of the first surfaces 631 (a first chamfering amount). Here, while an exemplary example in which each of the first surfaces 631 and the second surfaces 632 is a C surface has been provided, each of the first surfaces 631 and the second surfaces 632 may be an R surface. In addition, the first surface 631 is may be an R surface and the second surface 632 may be a C surface, or the first surface 631 may be a C surface and the second surface 632 may be an R surface.

Further, as shown in FIG. 1, the treatment tool main body 8 includes the operating wire 3, a binding part 40, a plurality of basket wires 2 and a distal end chip 41. The operating wire 3 is an elongated member extending along a longitudinal axis direction of the treatment tool main body 8, and inserted through the sheath 5 to advance and retract. A proximal end part of the operating wire 3 is connected to an engaging section. A basket 4 is provided on a distal end of the operating wire 3. In the embodiment, a stranded wire formed of a plurality of metal wires is used as the operating wire 3.

The plurality of basket wires 2 are elastic element wires that is elastically deformable and having an outer diameter smaller than a width of each of the first grooves 601 and the second grooves 602. The basket wires 2 are constituted by a single wire or a twisted wire formed of a material having high elasticity. The material of the basket wires 2 may be, for example, a nickel titanium alloy, a stainless steel, a stainless alloy, or the like.

Proximal end portions of the plurality of basket wires 2 are bundled by the binding part 40 and fixed to a distal end portion of the operating wire 3. The binding part 40 may employ a configuration in which the basket wires 2 are fixed to each other by using brazing, welding, caulking, resin welding, an adhesive agent and combinations thereof, or a configuration in which outer circumferential sides of the plurality of basket wires 2 are surrounded and fixed by a binding member. In the embodiment, the binding part 40 is configured by inserting the basket wires 2 through the tubular binding part 40 and fixing them by brazing.

Distal end portions of the basket wires 2 are bundled into one by the distal end chip 41 constituted by a pipe-shaped member. The distal end chip 41 has an insertion hole (not shown), the distal end portions of the plurality of basket wires 2 are inserted into the insertion hole, and the distal end portions of the basket wires 2 are fixed to the distal end chip 41 by using brazing, welding, caulking, resin welding, an adhesive agent and combinations thereof.

The basket wires 2 have a plurality of bent sections 20, preferably, from the distal end chip 41 to the binding part 40. Further, the basket wires 2 may be smoothly curved from the distal end chip 41 to the binding part 40 and the basket wires 2 may be not necessary to have the bent sections 20. The basket 4 is configured to be expanded in a basket shape in its natural state by the plurality of basket wires 2.

In the embodiment, while the basket is constituted by the four basket wires 2, the number of the basket wires may be appropriately set in consideration of ease of capture or difficulty of removal of a calculi.

In the treatment tool main body 8, the operating wire 3 is inserted through the sheath 5 to advance and retract, and a proximal end of the operating wire 3 is detachably connected to the engaging section of the operation section 7. The operating wire 3 advances and retracts with respect to the sheath 5 and the basket 4 protrudes from a distal end of the distal end cover 6 (a distal end of the sheath) according to a rotating operation of the handle 71 of the operation section 7.

Figure 6:
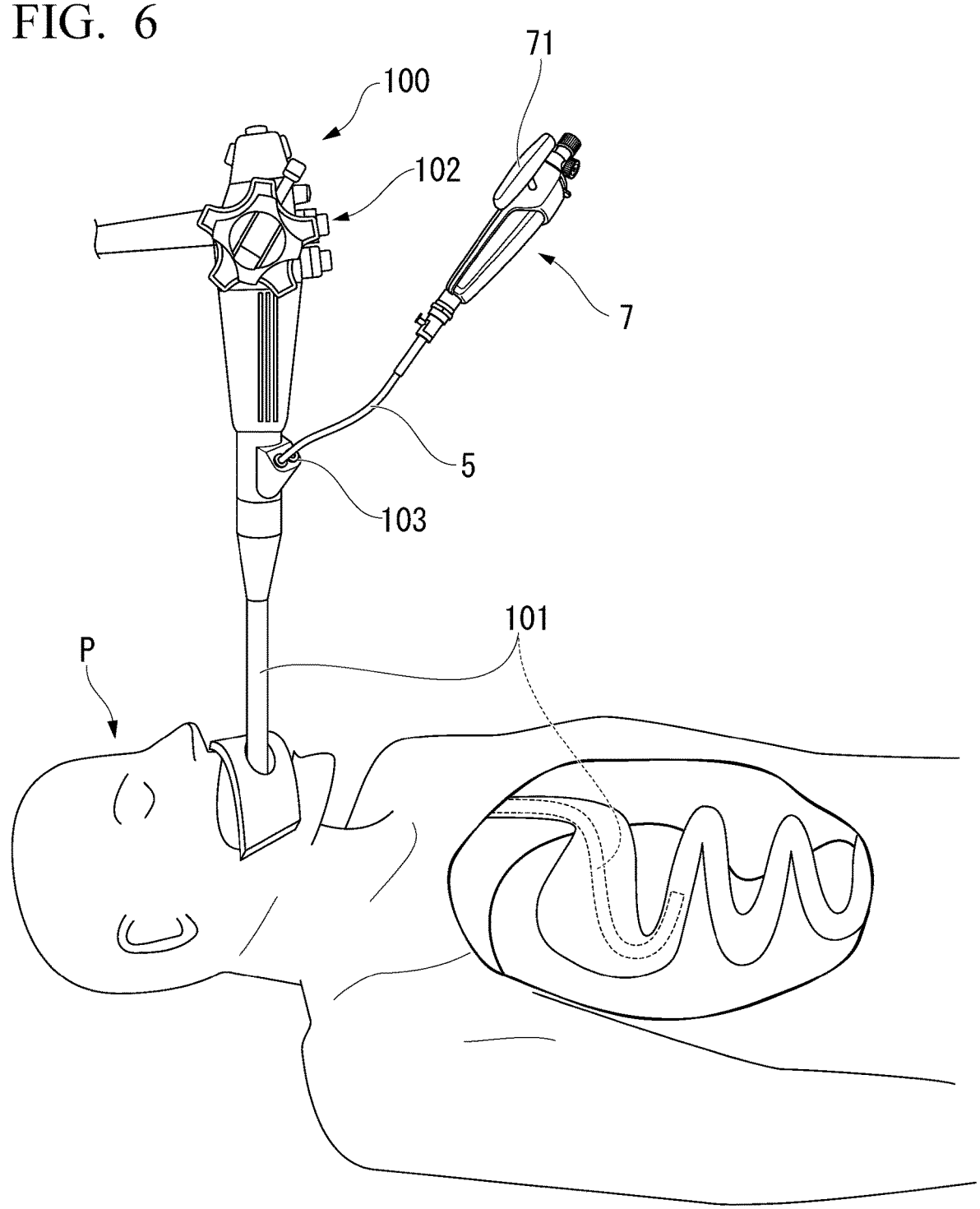
FIG. 6 is a view showing a manner of use of the basket type treatment tool of the embodiment of the present invention.
Figure 7:
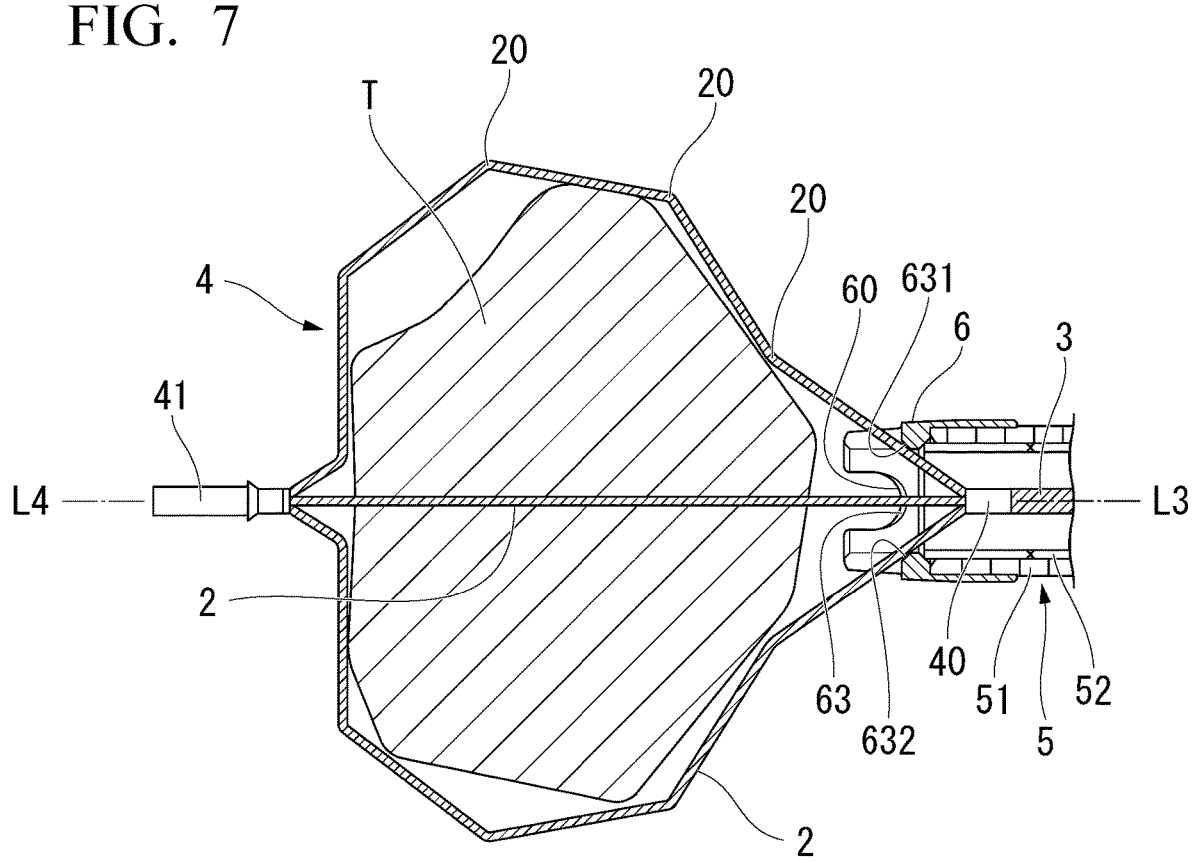
FIG. 7 is a view showing a manner of use of the basket type treatment tool of an exemplary embodiment.
Figure 8:
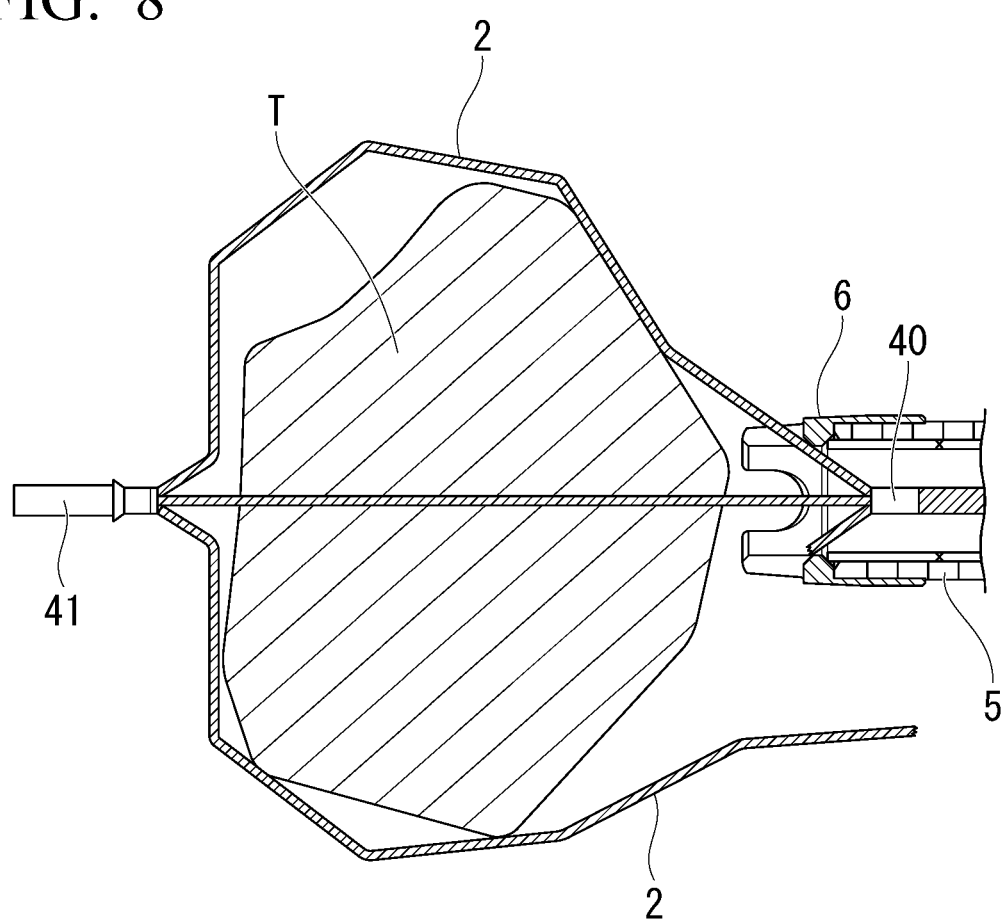
FIG. 8 is a view showing a manner of use of the basket type treatment tool of an exemplary embodiment.

An operation of the treatment tool 1 configured as above and a procedure using the treatment tool 1 will be described. Hereinafter, an exemplary procedure of removing foreign substances such as a calculi or the like generated in the bile duct will be described with reference to FIGS. 2 to 4 and 6. FIG. 6 is a view showing a manner of use of the treatment tool 1. FIGS. 7 and 8 are schematic views showing a state in which the treatment tool 1 is in use.

As shown in FIG. 6, the treatment tool 1 is used by being inserted into an endoscope insertion section 101 of an endoscope device 100. First, an operator inserts the endoscope insertion section 101 of the endoscope device 100 into the digestive canal from, for example, the mouth of a patient P, and inserts a distal end of the endoscope insertion section 101 into the duodenum while observing the insertion using an imaging means (not shown). Next, an operator inserts the treatment tool 1 into the endoscope insertion section 101 of the endoscope device 100 from an insertion port 103 and causes the distal end portion of the sheath 5 to protrude from the distal end of the endoscope insertion section 101. When the distal end portion of the sheath 5 protrudes, an endoscope operation section 102 of the endoscope device 100 is operated, and the sheath 5 is raised by an elevator (not shown) provided in the endoscope insertion section 101. An operator moves the sheath 5 forward with respect to the endoscope insertion section 101, causes the sheath 5 to enter inside the bile duct from a nipple, and inserts the sheath 5 until the distal end of the sheath 5 reaches the vicinity of a calculi T generated in the bile duct.

A proximal end portion of the operating wire 3 is inserted into the operation section main body 70 and connected to the operation section main body 70 according to an operation of the wire connecting button 72. Here, the basket 4 is accommodated in the sheath 5. While not shown, in a state in which the basket 4 is accommodated in the sheath 5, the basket 4 is pressed by an inner wall of a lumen of the sheath 5 and elastically deformed to reduce its diameter. Next, the operator grips the operation section main body 70 and operates the handle 71, and causes the basket 4 to protrude until the binding part 40 protrudes from the distal end cover 6 of the sheath 5. Here, the basket 4 is disposed on the side farther away than the calculi T.

FIG. 1 is a view showing a state in which the basket 4 is pushed out from the distal end of the sheath 5. In a state in which the basket 4 is pushed out from the distal end of the sheath 5 and no external force is applied to the basket 4, the basket 4 forms the basket 4 of a basis shape that is previously provided as show in FIG. 1 by a restoring force of the basket wires 2.

Next, when an operator operates to rotate the handle 71 to retract the basket 4, the neighboring basket wires 2 are stretched by the calculi T and the calculi T is captured in the basket 4. Since the calculi T is captured in the basket 4, an operator operates to rotate the handle 71 and the proximal end portion of the basket 4 is received in the sheath 5. Here, the calculi T is held by the plurality of basket wires 2 in a state in which the calculi T is received in a receiving section 26 of the basket 4. As shown in FIG. 7, the center axis L4 of the basket 4 is disposed substantially coaxially with the center axis L3 of the operating wire 3. For this reason, when the operating wire 3 is pulled and the basket 4 is immersed into the sheath 5, the basket wires 2 are pulled evenly while holding a state in which the center axis L4 of the basket 4 is disposed along the center axis L3 of the operating wire 3.

Next, when an operator operates to rotate the handle 71 to pull the operating wire 3 toward a proximal side, a force drawn into the sheath 5 is applied to the basket 4 and the calculi T is clamped by the basket 4. An operator continuously operates to rotate the handle 71 to pull the basket wires 2 toward the proximal side, and tightens and crushes the calculi T. The calculi T crushed by the above-mentioned series of procedure is discharged to the duodenum from the inside of the bile duct and finally discharged to the outside of the body.

Meanwhile, for example, as shown in FIG. 7, when a large and hard calculi T is received in the basket 4, the calculi T is stacked in the bile duct, and further, a state in which the calculi T cannot be crushed by the basket 4 (incarceration) occurs. In this case, when an operator continuously operates to rotate the handle 71, the operating wire 3 is pulled toward the proximal side, a force drawn into the sheath 5 is applied to the basket 4, and a state in which the calculi T is tightened by the plurality of basket wires 2 is provided.

Here, the basket wires 2 enter the grooves 60, respectively, and pulled toward the proximal side while coming into contact with the first surfaces 631 or the second surfaces 632 and applying a strong tensile force. Among the plurality of basket wires 2, stress is most concentrated to a portion of the basket wire 2 entering the second groove 602 which has a small chamfering amount and contacting with the second surfaces 632. For this reason, the basket wire 2 breaks earlier than the basket wire in contact with the first surfaces 631. That is, the basket wire 2 in contact with the second surfaces 632 breaks first (see FIG. 8). When breakage of the basket wire 2 in contact with the second surfaces 632 is recognized, an operator stops a rotational operation of the handle 71 and loosens pinching of the calculi T using the basket 4. After that, a wide gap is formed at a portion in which the basket wire 2 is broken, the calculi T drops out of the basket 4, and incarceration is solved. Here, since only the basket wire 2 in contact with the second surfaces 632, among the plurality of basket wires 2, is broken and the broken basket wire 2 is connected to the distal end chip 41 at a portion more distal side than the broken portion, it is possible to prevent the basket wires 2 from separating and dropping out of the treatment tool main body 8 after breakage. After the calculi T drops out of the basket 4, the sheath 5 and the treatment tool main body 8 are removed to the outside of the body from a proximal end side of the endoscope insertion section.

Further, when the calculi T accommodated in the basket 4 has a size and hardness such that a crushing process can be performed by the basket wires 2, the calculi T is crushed before reaching a breaking force at which the basket wires 2 breaks due to a contact with the slopes 63. That is, the basket wires 2 are set not to be broken even in contact with the second surfaces 632 in a state in which a predetermined tensile force is applied to the basket wires 2 by pulling the basket wires 2 while the calculi T is captured, the basket wires 2 are set to strength to be broken when the basket wires 2 come in contact with the second surfaces 632 in a state in which a force of the predetermined tensile force or more is added.

In the treatment tool 1 according to the embodiment, the plurality of grooves 60 corresponding to the number of the basket wires 2 are formed to be separated in the circumferential direction. The plurality of grooves 60 correspond to positions of the basket wires 2 such that the plurality of basket wires 2 do not enter one groove. For this reason, when the operating wire 3 is pulled toward the proximal side in a state in which the calculi T is accommodated therein, the basket wires 2 individually enter the grooves 60.

As a result, when the operating wire 3 is pulled toward the proximal side in a state in which a force of the predetermined tensile force or more is added, the basket wires 2 abut the slopes 63 on the side of the inner circumferential surface 62 of the distal end cover 6 in a state in which a strong tensile force is applied to the basket wires 2 that hold the calculi T in the basket 4 through the grooves 60. Here, since the slopes 63 of the grooves 60 have the first surfaces 631 and the second surfaces 632 having different chamfering shapes, a uniform tensile force is not applied to each of the basket wires 2, stress is concentrated to a part of the basket wire so as to be broken first. Accordingly, it is possible to prevent the plurality of basket wires 2 from being simultaneously broken and a part of the basket 4 on the distal side from dropping out of the body.

As a result, when incarceration is generated, some of the basket wires 2 are capable of being broken to remove the calculi T, and the entire the treatment tool main body 8 after some of the basket wires 2 are broken is capable of being removed from the sheath 5. That is, treatment upon incarceration can be smoothly and rapidly performed.

In the treatment tool 1 according to the embodiment, among the plurality of grooves 60, since a chamfering amount of the second surfaces 632 is smaller than a chamfering amount of the first surfaces 631, when the operating wire 3 is pulled toward the proximal side, a breaking force applied to the basket wire 2 in contact with the second surfaces 632 is increased to be larger than that of the basket wire 2 in contact with the first surfaces 631. Accordingly, when the operating wire 3 is pulled toward the proximal side upon generation of the incarceration, the basket wire 2 in contact with the second surfaces 632 are capable of being broken prior to the other basket wires 2.

In the treatment tool 1 according to the embodiment, since the chamfering amount of the second surfaces 632 (the second chamfering amount) is ½ or less of the chamfering amount of the first surfaces 631 (the first chamfering amount), a breaking force difference between the basket wire 2 in contact with the second surfaces 632 and the basket wire 2 in contact with the first surfaces 631 is capable of being increased. As a result, when the operating wire 3 is pulled toward the proximal side upon generation of the incarceration, the basket wire 2 in contact with the second surfaces 632 are capable of being more securely broken in advance.

Hereinabove, while the embodiment of the present invention has been described with reference to the accompanying drawings in detail, a specific configuration is not limited to the embodiment and may include design changes or the like without departing from the spirit of the present invention.

In addition, components shown in modified examples of the above-mentioned embodiment may be appropriately combined with each other. Hereinafter, while the modified examples or the like of the present invention have been described, the same as or similar to the parts, members, or the like, described in the above-mentioned embodiment are designated by the same reference numerals, and descriptions thereof will be omitted.

While an exemplary example in which the treatment tool 1 according to the embodiment has the two first grooves 601 and the two second grooves 602 has been provided, the treatment tool according to the present invention may have a configuration in which at least one groove having a different form of chamfering, among the plurality of grooves, is provided. For example, in the distal end cover having the four grooves, three grooves may be first grooves, and one groove may be a second groove.

Modified Example 1

Figure 9:
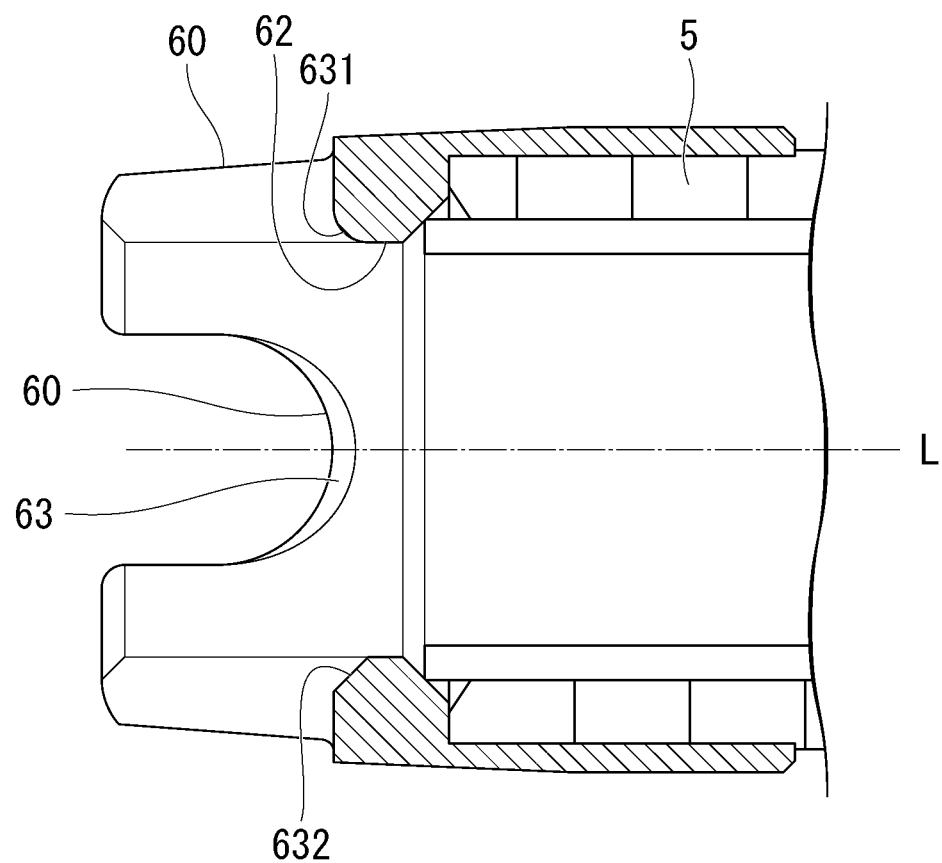
FIG. 9 is a cross-sectional view showing an example of a distal end chip of an exemplary embodiment.

A modified example of the distal end cover of the embodiment will be described. FIG. 9 is a schematic view showing a configuration of modified example 1 of the embodiment. As shown in FIG. 9, the modified example is an example in which a first surface 631A of a distal end cover 6A is an R surface, a second surface 632A is a C surface, and an inclination angle and a chamfering amount are the same. In the modified example, when the basket wires 2 come in contact with corner sections formed at boundaries between the second surfaces 632A and the bottom sections 61 or boundaries between the second surfaces 632A and the inner circumferential surfaces 62, stress is easily concentrated to contact positions thereof. Meanwhile, since the first surface 631 is the R surface and a corner section like the second surface 632A is not formed, the basket wires 2 are harder to be broken than the basket wires 2 passing through the second grooves 602. In this way, even when the chamfering amounts are the same as and shapes of the slopes 63A are different from each other, like the embodiment, stress concentration occurs on the basket wire 2 in contact with the second surface, and the basket wire 2 passing through the second groove 602 is cut earlier than the basket wire 2 passing through the first groove 601.

Modified Example 2

Figure 10:
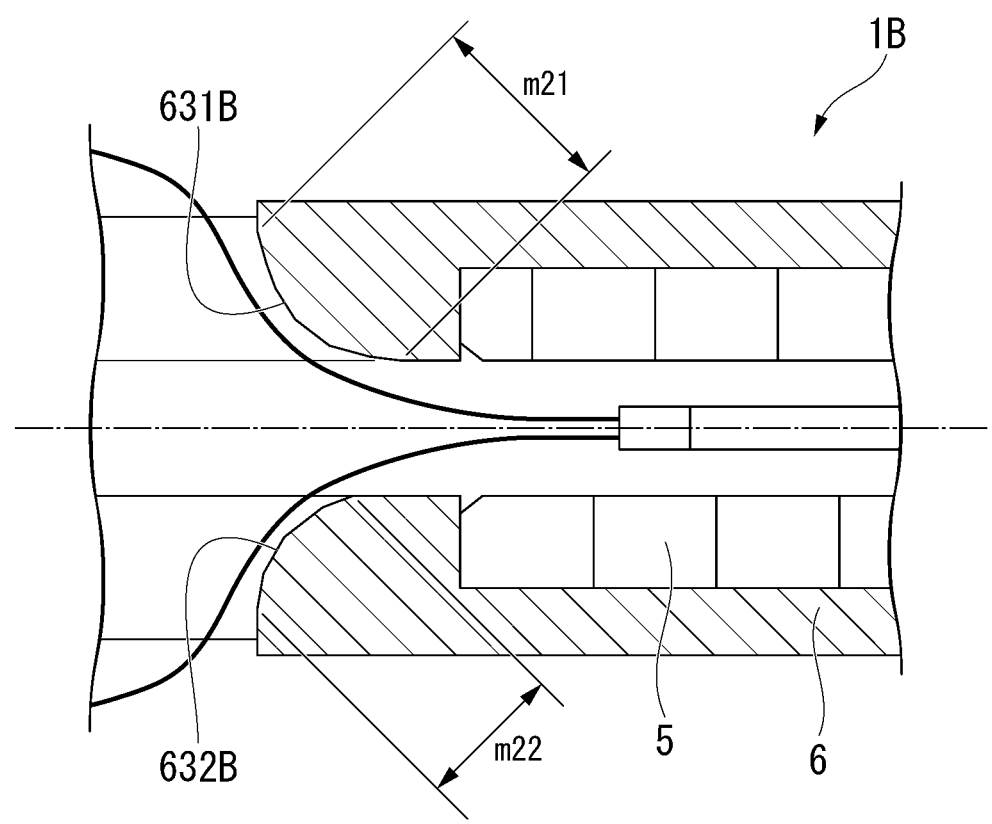
FIG. 10 is a cross-sectional view showing a modified example of the distal end chip of an exemplary embodiment.

FIG. 10 is a schematic view showing a configuration of modified example 2 of the distal end cover of the embodiment. Slopes of the distal end cover are not limited to the R surface and the C surface, and as shown in FIG. 10, may be a slope 63B in which C surfaces having slightly different inclination angles are continuously formed. The modified example shown in FIG. 10 is an example in which lengths m2 of the first surfaces 631B and the second surfaces 632B are different from each other. In the modified example, a length m22 of the second surfaces 632B is shorter than a length m21 of the first surfaces 631B. Accordingly, when a tensile force is applied to the basket wires 2, a breaking force that is larger at the basket wire 2 passing through the second groove 602B than at the basket wire 2 passing through the first groove 601B is applied, and the basket wire 2 in contact with the second surface 632B is broken first. As a result, the same effect as the embodiment is exhibited even in the modified example.

While the example in which the second surfaces 632 are formed in the two grooves among the four grooves of the distal end cover has been described in the embodiment, the number of the second surfaces is not limited thereto, and at least one first groove having a first surface and at least one groove having a second surface, among the plurality of grooves, may be provided. For example, a configuration in which three first grooves and one second groove, among the four grooves of the four distal end covers, are formed may be provided. In addition, even when five basket wires or more are provided, second grooves are more preferably formed at neighboring positions in the circumferential direction when the plurality of second grooves of the distal end cover are provided in that an effect of breaking some of the plurality of basket wires in advance is obtained. In addition, a distal end cover further including a groove that does not have a slope, in addition to the first groove and the second groove, may be provided.

While the example in which the number of the basket wires and the grooves of the distal end cover is four has been described in the embodiment and the modified example, the number of the basket wires and the grooves of the distal end cover is not limited thereto, the number of the basket wires may be set such that the basket accommodates a treatment object, and a configuration including three or more basket wires and grooves of the distal end cover may be provided.

The basket of the present invention is not limited to the shape shown in the embodiment, and a configuration having a basket shape constituted by a plurality of basket wires and configured to capture foreign substances may be provided.

A type of the basket wire according to the present invention is not limited to the embodiment. For example, a configuration in which each of the basket wires is one twisted wire at a proximal end side of the basket, the basket wire in which each of the basket wires is branched off into a plurality of wires at an intermediate portion of the basket and distal end portions of the basket wires are bundled by a distal end chip may be provided. In the treatment tool according to the present invention, since the basket wire is broken at a portion at which the basket wire closer to the proximal end than to the treatment object comes in contact with the second surface of the second groove of the distal end cover, the same effect as in the embodiment is obtained by forming at least one second surface.

What is claimed is:
1. A basket type treatment tool comprising:
   a sheath extending in a longitudinal axis direction;
   a distal end cover that is cylindrical and attached to a distal end of the sheath, the distal end cover including a plurality of grooves extending from an inner circumferential surface to an outer circumferential surface of the distal end cover, the grooves being concave;
   a plurality of basket wires that are configured to extend and retract from the distal end cover and configured to form a basket, the basket being configured to expand and contract according to extension and retraction from the distal end cover; and
   an operating wire connected to proximal ends of the plurality of basket wires and configured to advance from and retract into the sheath, wherein:
   the plurality of grooves includes a first groove and a second groove separate from the first groove in a circumferential direction of the distal end cover,
   the first groove has a first surface, the first surface having a first chamfering amount,
   the second groove has a second surface, the second surface having a second chamfering amount that is smaller than the first chamfering amount.

2. The basket type treatment tool according to claim 1, wherein among the plurality of basket wires, a basket wire in contact with the second surface is configured to break before a basket wire in contact with the first surface.

3. The basket type treatment tool according to claim 2, wherein the second chamfering amount is half of the first chamfering amount.

4. The basket treatment tool according to claim 2, wherein the second chamfering amount is less than half of the first chamfering amount.

5. The basket type treatment tool according to claim 1, wherein: the plurality of grooves includes at least two second grooves; and the second grooves neighbor each other in the circumferential direction.

6. The basket type treatment tool according to claim 1, wherein a number of the grooves is equal to a number of the basket wires.

7. The basket type treatment tool according to claim 1, wherein the first surface and the second surface are inclined from bottom surfaces of the first groove toward an inner circumferential surface of the distal end cover in a longitudinal axis direction of the distal end cover.

8. The basket type treatment tool according to claim 7, wherein: the second surface is chamfered such that a bottom surface of the second groove has a dimension different from the first surface.

9. The basket type treatment tool according to claim 1, wherein: when the operating wire is pulled in a direction from the distal end toward the proximal end of the sheath in a state in which a treatment object is accommodated in the basket, each of the plurality of basket wires is pulled through a different one of the plurality of groove sections, and a breaking force of one of the basket wires abutting on the first surface is different from one of the basket wires abutting on the second surface.

10. The basket type treatment tool according to claim 1, wherein when the operating wire is pulled from the distal end toward the proximal end of the sheath, each of the plurality of basket wires is pulled through a different one of the plurality of grooves and abuts one of the first surface and one of the second surface.

11. The basket treatment tool according to claim 1, wherein a portion of the second surface of the second groove has an inclination or a length different from the first surface.

12. The basket treatment tool according to claim 1, wherein the first surface that is inclined in a same direction as an incline of a portion of the basket wires when the basket protrudes from the distal end cover.

13. The basket treatment tool according to claim 1, wherein the second surface that inclined in a same direction as an incline of a portion of the basket wires when the basket protrudes from the distal end cover.

14. A basket type treatment tool comprising:
a sheath extending in a longitudinal axis direction;
a distal end cover that is cylindrical and configured to connect to a distal end of the sheath, the distal end cover including a plurality of grooves extending from an inner circumferential surface to an outer circumferential surface;
a plurality of basket wires that are configured to extend and retract from the distal end cover and configured to form a basket, the basket being configured to expand and contract according to extension and retraction from the distal end cover; and,
an operating wire connected to proximal ends of the plurality of basket wires and configured to advance from and retract into the sheath, wherein:
the plurality of grooves includes a first groove and a second groove separate from the first groove in a circumferential direction of the distal end cover,
the first groove has a first surface that is aligned with a portion of the basket wires when the basket protrudes from the distal end cover,
the second groove has a second surface that is aligned with a portion of the basket wires when the basket protrudes from the distal end cover,
the first surface and the second surface are provided in a same corresponding position in the first groove and the second groove, respectively, and
a portion of the second surface of the second groove has an inclination or a length that is different from the first surface.

\* \* \* \* \*